(12) United States Patent
Corcoran et al.

(10) Patent No.: US 7,966,886 B2
(45) Date of Patent: *Jun. 28, 2011

(54) METHOD AND APPARATUS FOR MEASURING PRESSURE INSIDE A FLUID SYSTEM

(75) Inventors: Kevin Corcoran, Mableton, GA (US); Florent Cros, Decatur, GA (US); Miguel Luis Berr, Las Condes (CL)

(73) Assignee: CardioMEMS, Inc., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/576,903

(22) Filed: Oct. 9, 2009

(65) Prior Publication Data

US 2010/0024561 A1      Feb. 4, 2010

Related U.S. Application Data

(63) Continuation of application No. 11/876,252, filed on Oct. 22, 2007, now Pat. No. 7,647,831.

(60) Provisional application No. 60/858,308, filed on Nov. 9, 2006, provisional application No. 60/853,131, filed on Oct. 20, 2006.

(51) Int. Cl.
    *G01L 7/00* (2006.01)
(52) U.S. Cl. .......................... 73/700; 600/561
(58) Field of Classification Search ................. None
    See application file for complete search history.

(56) References Cited

U.S. PATENT DOCUMENTS

| | | | | | |
|---|---|---|---|---|---|
| 5,363,855 | A | * | 11/1994 | Drzewiecki et al. | 600/485 |
| 5,797,879 | A | * | 8/1998 | DeCampli | 604/93.01 |
| 5,921,934 | A | * | 7/1999 | Teo | 600/468 |
| 5,967,986 | A | * | 10/1999 | Cimochowski et al. | 600/454 |
| 5,967,989 | A | * | 10/1999 | Cimochowski et al. | 600/459 |
| 6,015,386 | A | * | 1/2000 | Kensey et al. | 600/486 |
| 6,176,831 | B1 | * | 1/2001 | Voss et al. | 600/485 |
| 6,585,763 | B1 | * | 7/2003 | Keilman et al. | 623/1.42 |
| 7,427,265 | B1 | * | 9/2008 | Keilman et al. | 600/300 |
| 2005/0288604 | A1 | * | 12/2005 | Eigler et al. | 600/561 |
| 2005/0288722 | A1 | * | 12/2005 | Eigler et al. | 607/9 |
| 2007/0163353 | A1 | * | 7/2007 | Lec et al. | 73/700 |

* cited by examiner

*Primary Examiner* — Lisa M Caputo
*Assistant Examiner* — Jermaine Jenkins
(74) *Attorney, Agent, or Firm* — Ballard Spahr LLP

(57) ABSTRACT

A disclosed method determines fluid pressure inside a vessel without compromising the integrity of the vessel. A sensor is positioned in operative communication with the external wall of the vessel such that expansion of the external wall of the vessel exerts a force against the sensor that is directed substantially radially outward with respect to the vessel. A substantially radially inward force is caused to be directed against the sensor in response to the substantially radially outward force exerted by the external vessel wall. The sensor can thus be used to detect the magnitude of the substantially radially outward force, which can be used to determine the pressure of the fluid within the vessel.

15 Claims, 4 Drawing Sheets

METHOD AND APPARATUS FOR MEASURING PRESSURE INSIDE A FLUID SYSTEM

CROSS-REFERENCE TO RELATED APPLICATION

This application is a continuation of pending U.S. patent application Ser. No. 11/876,252, filed on Oct. 22, 2007, which claims priority to U.S. Provisional Application No. 60/858,308, filed on Nov. 9, 2006 and to U.S. Provisional Application No. 60/853,131, filed on Oct. 20, 2006, the entire disclosure of all of the above-reference applications being incorporated herein by reference.

TECHNICAL FIELD

The present invention relates generally to methods and apparatus for measuring hydraulic or pneumatic pressure and relates more specifically to a method and apparatus for measuring dynamic or static hydraulic or pneumatic pressure inside a fluid system by monitoring changes in stress or pressure states on the outside of a fluid system.

BACKGROUND OF THE INVENTION

In many industrial and biological environments, it is desirable to determine the characteristics of fluid internal to fluid systems without breaching the fluid-containing vessel. For example, it is desirable to measure blood pressure characteristics at various points in the organs and blood-carrying vessels without having to breach an organ or vessel surgically to place a pressure sensor directly in the fluid contained therein.

As one example, the assessment of patients with congestive heart failure (CHF) following cardiac surgery remains difficult. For up to six months following surgery, these patients undergo a complex shift in their fluid-volume status. In the outpatient setting, the management of these patients has been performed by a history of increasing shortness of breath and a physical examination entailing assessment of the extent of pedal edema. Currently, these measurements are indirect surrogates of a poorly functioning heart and do not provide objective data on cardiac hemodynamics including heart filling pressures and cardiac output. Another test commonly used to evaluate CHF is a chest X-ray. Unfortunately, this test also does not provide objective hemodynamic data. A Swan-Ganz catheter does provide cardiac hemodynamics and is routinely utilized during and immediately following cardiac surgery. However, it is unreasonable to perform this procedure on a routine basis in the outpatient setting for the necessary adjustment of medications related to CHF because of the danger and discomfort to which the patient is subjected. To date, there is very little non-invasive objective hemodynamic or cardiodynamic data following cardiac surgery that guides the proper management in this complex group of patients.

The availability of an implantable device with the capability of safe, non-invasive hemodynamic monitoring has the potential to change the landscape in the management of patients following cardiac surgery. Availability of such a device would greatly enhance CHF management, patient lifestyle and reduce unnecessary hospitalizations and costs to society, currently estimated at $38 billion/year. Moreover, the potential for life-long in-hospital and outpatient monitoring of these patients may significantly decrease risks associated with invasive hemodynamic monitoring and allow more succinct tailoring of heart failure medications. Furthermore, with a portable monitoring system, patients can be monitored at home, negating costs associated with readmissions and emergency room visits for patients with heart failure.

SUMMARY OF THE INVENTION

The assessment of pressure inside a fluid system by monitoring changes in stress or pressure states on the exterior of a fluid system (e.g., fluid carrying pipe or tubing, pressure vessel, organ, or a blood vessel—collectively referred to hereafter as a "vessel") using a wireless pressure sensor provides a valuable tool for sensing pressure non-invasively in harsh industrial environments or inside the human body without the need to open the fluid-containing vessel or organ. By eliminating the need to breach the fluid containing vessel, installation, be it mechanical or surgical, is greatly simplified. There is no risk of thromboembolitic event, either through clotting if a foreign body is placed in the fluid, or through the embolization of a foreign body (e.g., a sensor or piece of a sensor) as there would be if the sensor were placed within the vessel and directly in the fluid.

Stated somewhat more specifically, in a first aspect the present invention comprises a method for determining fluid pressure inside a vessel without compromising the integrity of the vessel. A sensor is positioned in operative communication with the external wall of the vessel such that expansion of the external wall of the vessel exerts a force against the sensor that is directed substantially radially outward with respect to the vessel. A substantially radially inward force is caused to be directed against the sensor in response to the substantially radially outward force exerted by the external vessel wall. The sensor can thus be used to detect the magnitude of the substantially radially outward force.

In a second aspect, the present invention comprises an apparatus for determining fluid pressure inside a vessel without compromising the integrity of the vessel. The apparatus includes a sensor and a band operatively associated with the sensor and configured to at least partially encircle the vessel so as to retain the sensor in operative communication against the external wall of the vessel. The band exerts a substantially radially inward force against the sensor in response to the substantially radially outward force exerted by the external vessel wall.

DETAILED DESCRIPTION OF THE DISCLOSED EMBODIMENTS

Figure 1:
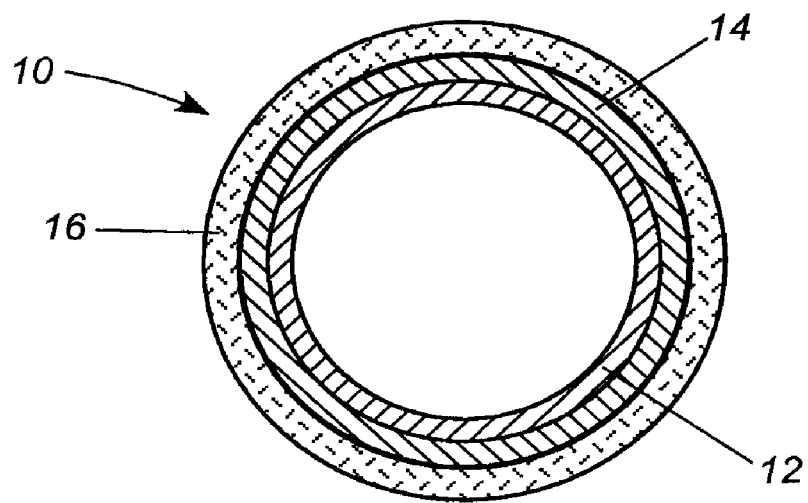
FIG. 1 is a cross-sectional view of a blood vessel of a human patient.

Referring now in more detail to the drawings, in which like numerals indicate like elements throughout the several views, FIG. 1 illustrates a blood vessel in the form of an artery 10 of a human patient. The artery 10 is composed of three layers, the innermost being the intima 12, the middle being the media 14, and the outermost being the adventitia 16. The adventitia 16 is easily dissected from the inner layers (i.e., the media 14 and the intima 12).

Figure 2:
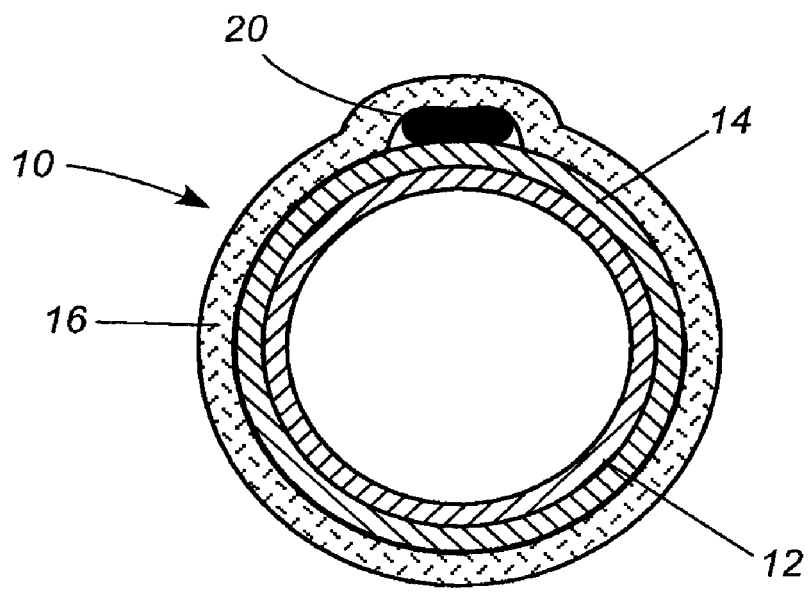
FIG. 2 is a cross-sectional view of the blood vessel of FIG. 1 showing a sensor located to sense pressure through the vessel wall.

As shown in FIG. 2, to determine hydrostatic pressure inside the artery 10, a sensor 20 is positioned just below the adventitia 16 but outside the media 14. Securing the sensor 20 immediately below the adventitia 16 and above the media 14 can be accomplished surgically by exposing the wall of the vessel 10, using a sharp object to make an incision through the adventitia 16 to the media 14. Then, using forceps to hold the incision open, the physician inserts the sensor 20 between the adventitia 16 and media 14. The sensor 20 can be pushed in between the layers, making its own space. Then, the incision is closed. The sensor packaging is biocompatible, and the vessel 10 heals around it, thus securing the sensor 20 without the need for additional securing means. If the sensor 20 remains securely placed and is subjected to reasonably constant stresses (other than changes in fluid pressure), the need for recalibration over time can be avoided. Then, fluid pressure can be determined by interrogating the sensor.

The stresses in the vessel wall change as a result of the fluid characteristics of the internal fluid. In turn, the electrical characteristics of the sensor 20 are influenced by the stresses in the vessel wall. When interrogated, the wireless sensor 20 transmits an RF signal to an external receiver that corresponds to a fluid pressure. An interrogating scheme such as that described in U.S. patent application Ser. Nos. 11/276,571 and 11/105,294 can be used to determine and track changes in these electrical characteristics, correlating them, ultimately, to pressure and other characteristics of the fluid (e.g., output values, temperature).

Pressure sensors suitable for the present application include, but are not limited to, sensors such as those described in U.S. patent application Ser. No. 10/054,671, filed on Jan. 22, 2002; U.S. patent application Ser. No. 10/886,829, filed on Jan. 22, 2002; U.S. patent application Ser. No. 10/215,377, filed on Aug. 7, 2002; U.S. patent application Ser. No. 10/215,379, filed on Aug. 7, 2002; U.S. patent application Ser. No. 10/943,772, filed on Sep. 16, 2004; U.S. patent application Ser. No. 11/157,375, filed on Jun. 21, 2005; U.S. Pat. No. 6,926,670; U.S. Pat. No. 6,926,670; and U.S. Pat. No. 7,073,387, all of which are hereby incorporated by reference in their entireties.

As an example of a sensor 20 that is suitable for the present invention, a sensor includes a housing defining a chamber and having a deflectable exterior wall portion that serves as a "sensing surface." Capacitor and inductor elements within the chamber form an LC circuit. A first capacitor element is coupled to the deflectable wall portion. As the wall deflects in response to changes in ambient pressure, the first capacitor is displaced with respect to the second capacitor, thereby changing the capacitance of the circuit. The resonant frequency of the LC circuit thus changes. This change in the resonant frequency of the LC circuit can be detected by interrogating the sensor. More specifically, the sensor is electromagnetically coupled to an external transmitter, which induces a current in the LC circuit that oscillates at the resonant frequency of the sensor. This oscillation causes a change in the frequency spectrum of the transmitted signal. From this change, the bandwidth and resonant frequency of the sensor can be determined, and an associated pressure can be established.

The sensor 20 is placed in operative communication with the external wall of a fluid-carrying vessel, either by placing the sensing surface of the sensor directly against the external wall of the vessel or by placing the sensing surface against an intervening element that transmits pressure changes from the vessel wall to the sensing surface. The sensor 20 is thus able to detect changes in pressure of the fluid flowing within the vessel. In the context of a biomedical application, the sensor 20 can be placed in conductive communication with the wall of a blood vessel. When the blood pushes on the wall of the vessel, a radially outward force is exerted by the vessel wall. The sensor senses the change in pressure. The tissue backing the sensor exerts a radially inward force in opposition to the radially outward force exerted by the vessel wall. The sensor can be embedded within the vessel wall, fixed directly to the outside of the vessel wall, or fixed to a layer of tissue (e.g., fat) that is in direct contact with the vessel wall.

Polymer-metal, polymer-ceramic, biological tissue-metal and biological tissue-ceramic interfaces of the vessel wall-sensing surface are particularly suited to the present application.

Figure 3:
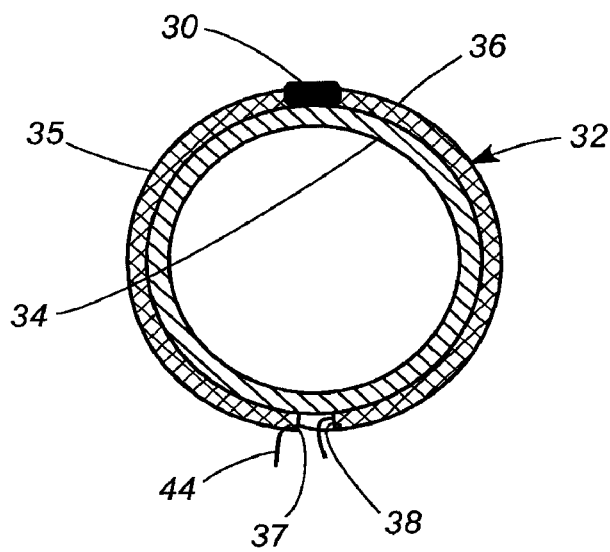
FIG. 3 is a cross-sectional view of a vessel having a sensor secured to the vessel wall by means of a band.

FIG. 3 illustrates an alternative embodiment in which a sensor 30 is supplied with a band 32 to secure it to the periphery of a vessel 34. The band 32 of the disclosed embodiment is manufactured from a material that is flexible and substantially nonextensible, for example, a biocompatible polymer (e.g., PTFE). The band 32 has two band portions 35, 36. Each band portion is joined at one end to the sensor 30. The vessel 34 is exposed, and a sensing surface 40 of the sensor 30 is placed in contact with the outer vessel wall 42. The ends 37, 38 of the polymer band portions 35, 36 are wrapped around the vessel and secured together with a suture 44 or other suitable fastener (e.g., adhesive, snap, button, staple, etc.) to anchor the sensor 30 to the vessel 34. When the vessel wall exerts a radially outward force in response to an increase in fluid pressure within the vessel, the band 32 exerts a radially inward force against the sensor 30. The increase in force causes changes to the electrical characteristics of the sensor, and these electrical characteristics can be detected and correlated to pressure changes within the vessel.

In the alternative, the band 32 can be formed as a single, continuous component to which the sensor is attached, rather than two separate band portions, with the free ends of the band 32 wrapped around the vessel and secured.

Figure 4:
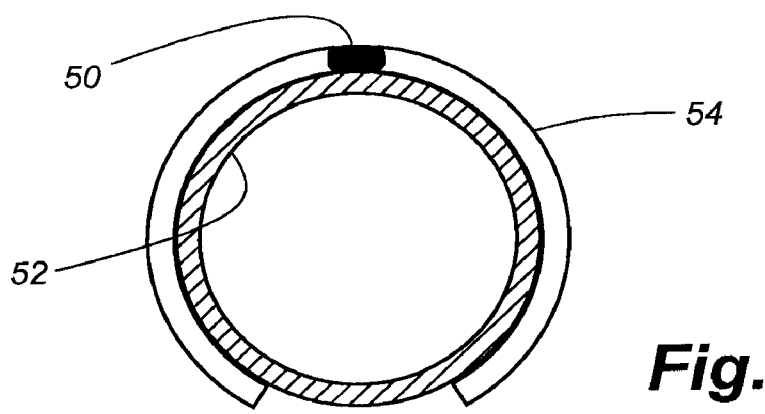
FIG. 4 is a cross-sectional view of a vessel having a sensor secured to the vessel wall by means of an alternate embodiment of a band.

FIG. 4 depicts another embodiment, in which a sensor 50 is held in position against the wall of a vessel 52 by a C-shaped partial ring 54. The pliable vessel 52 is worked through the opening of the partial ring 54. Alternately the partial ring 54 can be fabricated from a shape-memory metal or alloy (e.g. nitinol). In this latter case, the partial ring 54 can be configured to close around the vessel 52 by shape memory effects after the ring has been implanted.

Figure 5:
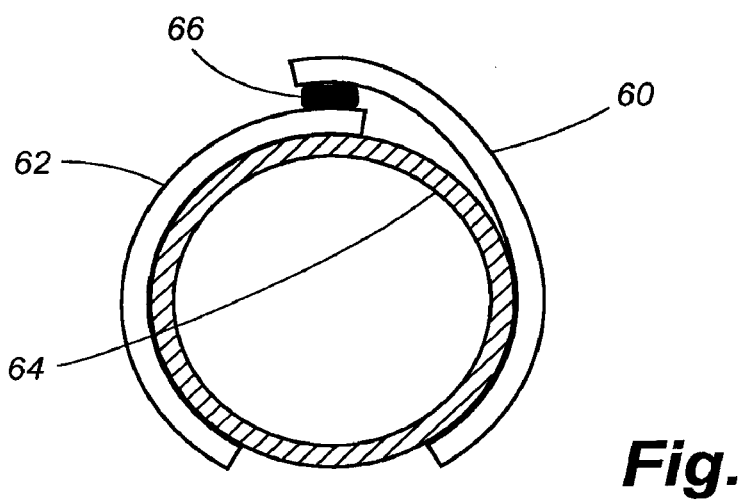
FIG. 5 is a cross-sectional view of a vessel having a sensor secured to the vessel wall by means of a further embodiment of a band in which two band elements act as levers.

FIG. 5 illustrates a further embodiment, in which two metal bands 60, 62 are used to create a lever by which a change in the fluid pressure within a vessel 64 is communicated to a sensor 66. A first band 60 is secured to the side of the sensor 66 opposite the surface in contact with the vessel wall, and the second band 62 is secured to the side of the sensor 66 in contact with the vessel wall. When the vessel 64 changes diameter with a change in blood flow, the first and second bands 60, 62 pivot and act as a lever to compress or expand, thereby changing the electrical characteristics of the sensor 66.

Figure 6:
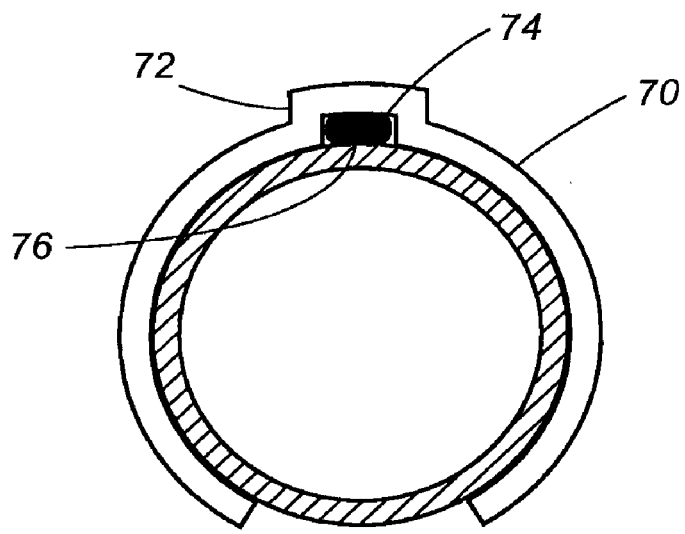
FIG. 6 is a cross-sectional view of a vessel having a sensor secured to the vessel wall by means of a band having a cradle for receiving the sensor.

FIG. 6 shows a band 70 comprising a cradle 72 in which a sensor 74 can be placed. The cradle 72 surrounds the top and sides of the sensor 74, leaving only the sensing surface 76 of the sensor exposed. The cradle 72 eliminates the need to recalibrate the sensor 74 if the stress exerted on the sensor from the environment surrounding the non-sensing surface changes appreciably over time.

Figure 7:
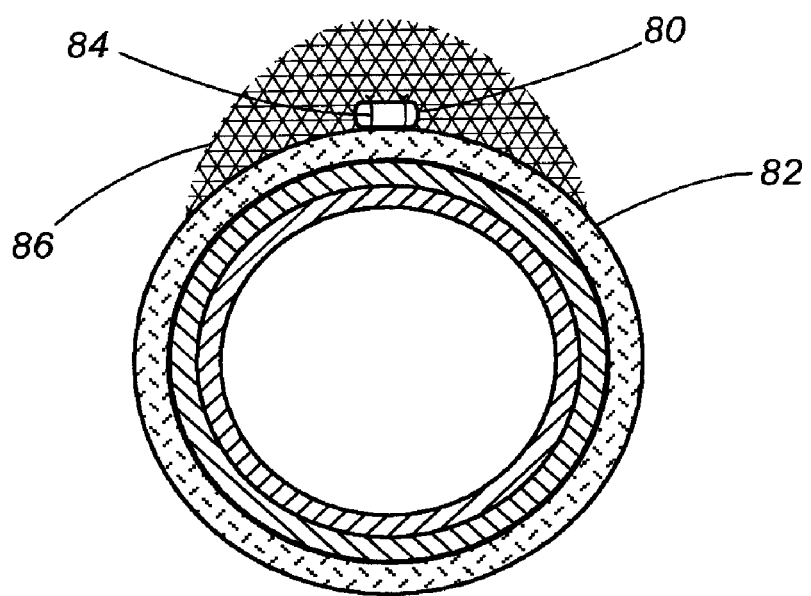
FIG. 7 is a cross-sectional view of an artery having a sensor sutured to the outer layers of the artery without penetrating the intima.

Referring now to FIG. 7, in yet another embodiment a sensor 80 is sutured to the outside of a vessel 82. The sutures 84 are superficial and do not puncture the vessel or organ (e.g., if secured to an artery, the stitches do not puncture the intima).

If the sensor 80 were only sutured to the vessel 82, without more, the sensor would simply move with the vessel wall as it expands or contracts. However, the sensor is backed by surrounding tissue 86, e.g., muscle or fat, which exerts a radially inward force with respect to the vessel 82 as the vessel expands or contracts. (It will be understood that the vessel 82 is completely surrounded by tissue 86, but only a portion of the tissue is shown in FIG. 7 for clarity of illustration). Thus the sensor housing is prevented from substantial movement, and the sensing surface of the sensor can measure the applied force.

Figure 8:
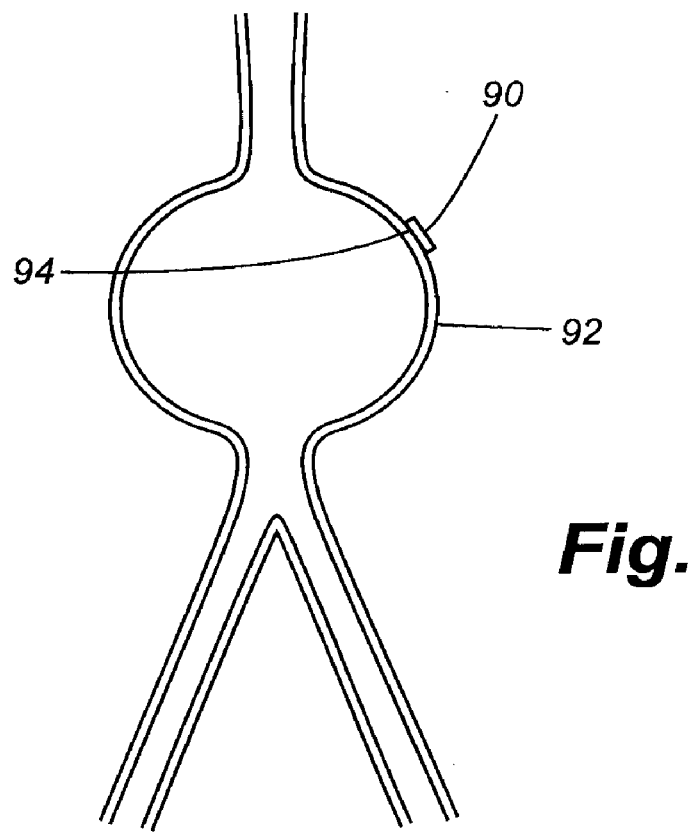
FIG. 8 is a cross-sectional view of an aneurysm having a sensor sutured to the outer vessel wall.

As yet another alternative embodiment, shown in FIG. 8, an adhesive can be used to secure a sensor 90 to the outside of the vessel. For example, a sensor 90 can be secured via a biocompatible adhesive to the exterior of a radial artery or to the exterior of an aneurysm 92. Again, the sensor is backed by surrounding tissue (not shown) and is prevented from substantial radially outward movement when the aneurysm 92 attempts to expand. The sensing surface 94 of the sensor 90 is thereby capable of detecting the applied force resulting from an increase in pressure inside the aneurysm 92.

Figure 9:
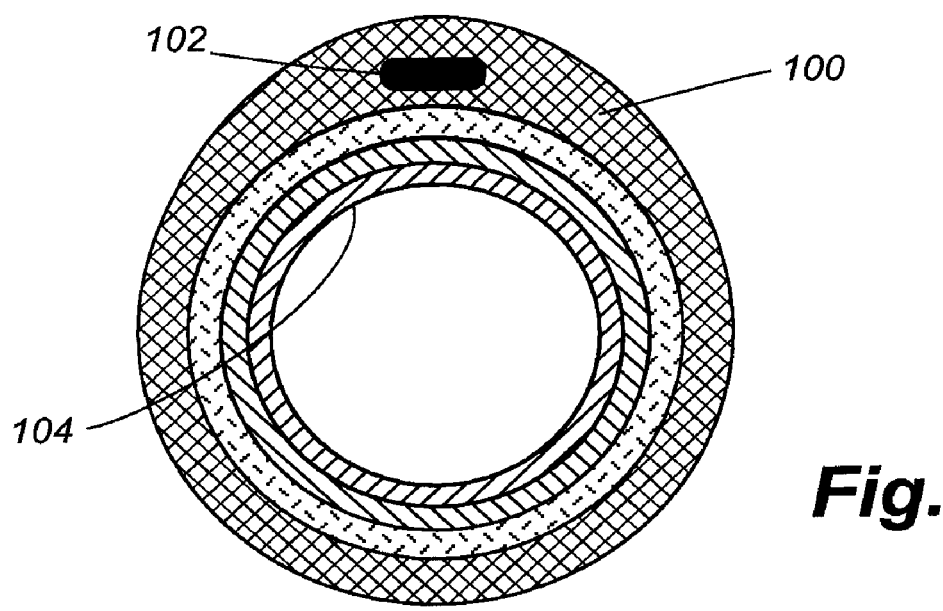
FIG. 9 is a cross-sectional view of an artery in which a sensor is secured just below the visceral pericardium but outside the artery.

Another example of using a sensor to determine hydrostatic pressure inside an artery in a human patient is to secure the sensor just below the visceral pericardium but outside the artery as shown in FIG. 9. The visceral pericardium 100 is the inner layer of the pericardium, a conical sac of fibrous tissue that surrounds the heart and the roots of the great blood vessels. Securing the sensor 102 immediately below the visceral pericardium 100 and above the artery 104 can be accomplished surgically by exposing the visceral pericardium, using a sharp object to make an incision through the visceral pericardium to the wall of the vessel 104, using forceps to hold the incision open and the blunt end of closed scissors to dissect a pocket under the visceral pericardium, and inserting the sensor 102 between the artery 104 and visceral pericardium 100. Then, the incision is closed. This method is extremely advantageous because the artery wall is not breached, even in part.

In each of the foregoing biological applications, the sensor packaging is biocompatible, and the vessel heals around it, thus securing the sensor without the need for additional securing means. The sensor remains securely placed, and reasonably constant stresses (other than fluid pressure) are exerted on the sensor to avoid the need for recalibration over time. Then, fluid pressure can be determined by interrogating the sensor as previously explained.

In the above biological examples, the sensors can be delivered and secured to the vessel by transcatheter delivery or open surgical techniques. These techniques are well within the level of skill of those practiced in the art, requiring only standard surgical procedures.

Outside of the realm of medicine, the same pressure sensors can be used as described above to sense stress on the exterior of vessels to determine the pressure and other characteristics of the fluid. The sensor could be installed on vessels that contain fluids and the pressure within those vessels monitored wirelessly. This is useful in harsh industrial environments (e.g., extreme temperatures, dangerous chemical environments). The sensors described in U.S. Pat. Nos. 6,111,520 and 6,278,379, incorporated in their entireties by reference, are particularly suitable for such industrial applications.

Furthermore, this invention can be practiced using a multitude of wireless sensing schemes, such as ultrasonic sensing.

Finally, it will be understood that the preferred embodiment has been disclosed by way of example, and that other modifications may occur to those skilled in the art without departing from the scope and spirit of the appended claims.

What is claimed is:

1. A method for determining fluid pressure inside a lumen defined by a vessel without compromising the integrity of the vessel, comprising the steps of:
    positioning a sensor in operative communication with the external wall of the vessel such that expansion of the external wall of the vessel exerts a force against the sensor that is directed substantially radially outward with respect to the vessel;
    causing a substantially radially inward force to be directed against the sensor in response to the substantially radially outward force exerted by the external vessel wall;
    using the sensor to detect the magnitude of the substantially radially outward force; and
    determining the fluid pressure within the lumen of the vessel from the detected magnitude of the substantially radially outward force.

2. The method of claim 1, wherein the step of causing a substantially radially inward force to be directed against the sensor in response to the substantially radially outward force exerted by the external vessel wall comprises the step of securing the sensor to the vessel with a band that at least partially encircles the vessel.

3. The method of claim 2, wherein the step of securing the sensor with a band that at least partially encircles the vessel comprises the step of securing the sensor with a band that completely encircles the vessel.

4. The method of claim 1, wherein the step of causing a substantially radially inward force to be directed against the sensor in response to the substantially radially outward force exerted by the external vessel wall comprises the step of inserting the sensor between the external wall of the vessel and an adjacent body of tissue.

5. The method of claim 4, wherein the vessel is an artery, and wherein the step of inserting the sensor between the external wall of the vessel and an adjacent body of tissue comprises the step of inserting the sensor just below the adventitia of the artery but outside the media of the artery.

6. The method of claim 4, wherein the vessel is an aneurysm.

7. The method of claim 4, wherein the vessel runs through the visceral pericardium, and wherein the step of inserting the sensor between the external wall of the vessel and an adjacent body of tissue comprises the step of inserting the sensor outside the vessel and within the visceral pericardium.

8. An apparatus for determining fluid pressure inside a lumen defined by a vessel without compromising the integrity of the vessel, wherein an increase in fluid pressure within the lumen of the vessel causes the external wall of the vessel to exert a radially outward force, the apparatus comprising:

a sensor;

a band operatively associated with the sensor and configured to at least partially encircle the vessel so as to retain the sensor in operative communication against the external wall of the vessel, wherein the band exerts a radially inward force on the sensor in opposition to the radially outward force exerted by the external wall of the vessel;

the sensor further comprising means for detecting the magnitude of the substantially radially outward force; and further comprising means for determining the fluid pressure within the lumen of the vessel from the detected magnitude of the substantially radially outward force.

9. The apparatus of claim 8, wherein the band completely encircles the vessel.

10. The apparatus of claim 8, wherein said band comprises a pair of band portions, each having a first end secured to the sensor, and a second end configured to at least partially encircle the vessel.

11. The apparatus of claim 8, wherein the band is flexible and substantially non-extensible.

12. The apparatus of claim 8, wherein the band is substantially rigid.

13. The apparatus of claim 8, wherein the band is formed from a shape-memory material.

14. The apparatus of claim 8 wherein the sensor comprises a sensing surface, and wherein the band is configured to retain the sensing surface of the sensor directly against the external wall of the vessel.

15. The apparatus of claim 8 wherein the sensor comprises a sensing surface, and wherein the band is configured to retain the sensing surface of the sensor against an intervening element that is in contact with the external wall of the vessel.

* * * * *